US006441132B1

(12) United States Patent
Jimenez et al.

(10) Patent No.: US 6,441,132 B1
(45) Date of Patent: Aug. 27, 2002

(54) CONTRYPHAN PEPTIDES

(75) Inventors: Elsie C. Jimenez, Quezon City (PH); Baldomero M. Olivera, Salt Lake City, UT (US); William R. Gray, Salt Lake City, UT (US); Lourdes Cruz, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/297,771

(22) PCT Filed: Nov. 7, 1997

(86) PCT No.: PCT/US97/20534

§ 371 (c)(1),
(2), (4) Date: Dec. 14, 1999

(87) PCT Pub. No.: WO98/20026

PCT Pub. Date: May 14, 1998

Related U.S. Application Data (60) Provisional application No. 60/030,722, filed on Nov. 8, 1996.

(51) Int. Cl.[7] .............................. C07K 4/12; C07K 7/00
(52) U.S. Cl. .................. 530/328; 514/16; 435/70.1; 435/70.3
(58) Field of Search ................... 530/328; 514/16; 435/70.1, 70.3

(56) References Cited

U.S. PATENT DOCUMENTS 5,514,774 A * 5/1996 Olivera et al.
6,077,934 A * 1/2000 Jacobsen et al. ............ 530/328

OTHER PUBLICATIONS

Jimenez et al., 'Contryphan is a D–Tryptophan–Containing Conus Peptide', J. of Biol. Chemistry vol. 271, No. 45, pp. 28002–28005. Nov. 8, 1996.*

* cited by examiner

*Primary Examiner*—Christopher S. F. Low
*Assistant Examiner*—Anish Gupta
(74) *Attorney, Agent, or Firm*—Rothwell, Figg, Ernst & Manbeck, P.C.

(57) ABSTRACT

The present invention is directed to contryphan peptides having 6–12 amino acids, preferably including one or more D-tryptophan residues. More specifically, the present invention is directed to contryphan peptides having the general formula $Xaa_1$-Cys-$Xaa_2$-$Xaa_3$-Glu-Pro-Trp-Cys (SEQ ID NO:1), wherein $Xaa_1$ is Gly or des-$Xaa_1$, $Xaa_2$ is Pro or 4-trans-hydroxyproline and $Xaa_3$ is D-Trp or L-Trp, preferably D-Trp. The present invention is further directed to the peptides contryphan R and des-Gly[1] contryphan R. In contryphan R, $Xaa_1$ is Gly and $Xaa_3$ is D-Trp. These contryphans are useful as anticonvulsant or neuroprotective agents.

8 Claims, 4 Drawing Sheets

SEQUENCE LISTING

<160> NUMBER OF SEQ ID NOS: 5

<210> SEQ ID NO 1
<211> LENGTH: 8
<212> TYPE: PRT
<213> ORGANISM: generic contryphan

```
<220> FEATURE:
<221> NAME/KEY: PEPTIDE
<222> LOCATION: (1)..(4)
<223> OTHER INFORMATION: Xaa at residue 1 is Gly or des-Xaa; Xaa at
      residue 3 is Pro or 4- trans-hydroxy-Pro; Xaa at residue 4 is
      L-Trp or D-Trp

<400> SEQUENCE: 1

Xaa Cys Xaa Xaa Glu Pro Trp Cys
1               5

<210> SEQ ID NO 2
<211> LENGTH: 8
<212> TYPE: PRT
<213> ORGANISM: Conus radiatus
<220> FEATURE:
<221> NAME/KEY: PEPTIDE
<222> LOCATION: (3)..(3)
<223> OTHER INFORMATION: Xaa at residue 3 is 4-trans-hydroxy-Pro

<400> SEQUENCE: 2

Gly Cys Xaa Trp Glu Pro Trp Cys
1               5

<210> SEQ ID NO 3
<211> LENGTH: 7
<212> TYPE: PRT
<213> ORGANISM: Conus radiatus
<220> FEATURE:
<221> NAME/KEY: PEPTIDE
<222> LOCATION: (2)..(2)
<223> OTHER INFORMATION: Xaa at residue 2 is Pro or 4-trans-hydroxy-Pro

<400> SEQUENCE: 3

Cys Xaa Trp Glu Pro Trp Cys
1               5

<210> SEQ ID NO 4
<211> LENGTH: 8
<212> TYPE: PRT
<213> ORGANISM: Conus radiatus
<220> FEATURE:
<221> NAME/KEY: PEPTIDE
<222> LOCATION: (2)..(3)
<223> OTHER INFORMATION: Xaa at residue 3 is Pro or 4-trans-hydroxy-Pro;
      Xaa at residue 4 is L-Trp or D-Trp

<400> SEQUENCE: 4

Gly Cys Xaa Xaa Glu Pro Trp Cys
1               5

<210> SEQ ID NO 5
<211> LENGTH: 7
<212> TYPE: PRT
<213> ORGANISM: Conus radiatus
<220> FEATURE:
<221> NAME/KEY: PEPTIDE
<222> LOCATION: (2)..(3)
<223> OTHER INFORMATION: Xaa at residue 2 is Pro or 4-trans-hydroxy-Pro;
      Xaa at residue 3 is L-Trp or D-Trp

<400> SEQUENCE: 5

Cys Xaa Xaa Glu Pro Trp Cys
1               5
```

CONTRYPHAN PEPTIDES

This application is a 371 of PCT/US97/20534 filed Nov. 7, 1997 and claims benefit of provisional appln. No. 60/030,722 filed Nov. 8, 1996.

This invention was made with Government support under Grant No. GM48677 awarded by the National Institute of General Medical Sciences, National Institutes of Health, Bethesda, Md. The United States Government has certain rights in the invention.

BACKGROUND OF THE INVENTION

This invention relates to relatively short peptides about 6–12 residues in length, which are naturally available in minute amounts in the venom of the cone snails or analogous to the naturally available peptides, and which include one or more D-tryptophan residues.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Mollusks of the genus Conus produce a highly toxic venom that enables them to carry out their unique predatory lifestyle. Prey are immobilized by the venom that is injected by means of a highly specialized venom apparatus, a disposable hollow tooth that functions both in the manner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al.. 1987). In addition, peptides named conantokins have been isolated from the Conus geographus and Conus tulipa (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990).

The standard amino acids in polypeptides translated from genes are exclusively in the L-configuration. In recent years it has been established that D-amino acids can be post-translationally introduced into such polypeptides (Kriel, 1994). Several small peptides have been characterized which contain a D-amino acid. The first of these was dermorphin, a potent heptapeptide agonist of the m-opiate receptor from amphibian skin, discovered by Erspamer and co-workers (Monteccuchi et al., 1981). A number of other peptides from amphibian skin (including the deltorphins and bombinin-H) were also found to have a D-amino acid. The cDNAs encoding these peptides were characterized (Richter et al., 1987; Richter et al., 1990). The results demonstrated unequivocally the presence of mRNA encoding the peptide precursor, indicating that the D-amino acid was post-translationally formed from the corresponding L-isomer.

In addition to these vertebrate systems, small peptides with D-amino acids have also been described in invertebrate systems, primarily molluscs. An FRMFamide analog from the bivalve, *Mytilus edulis,* which contains a D-leucine has been characterized (Fujisawa et al., 1992). Likewise, the land snail *Achatina fulica* has D-amino acid-containing small peptides, achatin-I and fulicin (Kamatani et al., 1989; Ohta et al., 1991). The cDNA encoding the precursor of fulicin was found to contain the usual L-Asn codon at the D-Asn position (Yasuda-Kamatani et al., 1995). Recently, the post-translational inversion of an amino acid was demonstrated in vitro for ω-agatoxin-IVB (also termed ω-agatoxin-TK), a Ca channel inhibitor from funnel web spider (Shikata et al., 1995). The peptide isomerase that preferentially acts on $Ser^{46}$ of the 48-amino acid peptide has been isolated and characterized.

Although there is no homology between vertebrate and invertebrate peptides (and the three molluscan peptides exhibit no sequence similarity), in every case the D-amino acid is found in the second position. This suggests that for small D-amino acid-containing peptides, the proteolytic event which generates the mature peptide and the post-translational enzymatic system which converts an L- to a D-amino acid work in combination to always generate the D-amino acid at position 2.

Epilepsy is a recurrent paroxysmal disorder of cerebral function characterized by sudden brief attacks of altered consciousness, motor activity, sensory phenomena or inappropriate behavior caused by abnormal excessive discharge of cerebral neurons. Convulsive seizures, the most common form of attacks, begin with loss of consciousness and motor control, and tonic or clonic jerking of all extremities, but any recurrent seizure pattern may be termed epilepsy. The term primary or idiopathic epilepsy denotes those cases where no cause for the seizures can be identified. Secondary or symptomatic epilepsy designates the disorder when it is associated with such factors as trauma, neoplasm, infection, developmental abnormalities, cerebrovascular disease, or various metabolic conditions. Epileptic seizures are classified as partial seizures (focal, local seizures) or generalized seizures (convulsive or nonconvulsive). Classes of partial seizures include simple partial seizures, complex partial seizures and partial seizures secondarily generalized. Classes of generalized seizures include absence seizures, atypical absence seizures, myoclonic seizures, clonic seizures, tonic seizures, tonic-clonic seizures (grand mal) and atonic seizures. Therapeutics having anticonvulsant properties are used in the treatment of seizures. Most therapeutics used to abolish or attenuate seizures demonstrate activity at least through effects that reduce the spread of excitation from seizure foci and prevent detonation and disruption of function of normal aggregates of neurons. Anticonvulsants which have been utilized include phenytoin, phenobarbital, primidone, carbamazepine, ethosuximide, clonazepam and valproate. For further details of seizures and their therapy (see Rall & Schleifer (1985) and *The Merck Manual* (1992)).

It has been shown that neurotransmission mediated through the NMDA receptor complex is associated with seizures (Bowyer, 1982; McNamara et al., 1988), ischemic neuronal injury (Simon et al., 1984; Park et al., 1988) and other phenomena including synaptogenesis (Cline et al., 1987), spatial learning (Morris et al., 1986) and long-term potentiation (Collinridge et al., 1983; Harris et al., 1984; Morris et al., 1986). Regulation of these -neuronal mechanisms by NMDA-mediated processes may involve activation of a receptor-gated calcium ion channel (Nowak et al., 1984; Mayer et al., 1987; Ascher and Nowak, 1988).

The NMDA channel is regulated by glycine. This amino acid increases NMDA-evoked currents in various tissues (Johnson and Ascher, 1987; Kleckner and Dingledine, 1988) by increasing the opening frequency of the NMDA channel (Johnson and Ascher, 1987). Thus, NMDA-induced calcium influx and intracellular accumulation may be stimulated by glycine (Reynolds et al., 1987; Wroblewski et al., 1989), which interacts with its own distinct site (Williams et al., 1991). Furthermore, accumulation of intracellular calcium may be implicated in the aforementioned neuropathologies.

It is desired to identify additional peptides which target the NMDA receptor. It is further desired to identify compounds which are useful as anticonvulsant or neuroprotective agents.

SUMMARY OF THE INVENTION

The present invention is directed to contryphan peptides having 6–12 amino acids, preferably including one or more D-tryptophan residues. More specifically, the present invention is directed to contryphan peptides having the general formula $Xaa_1$-Cys-$Xaa_2$-$Xaa_3$-Glu-Pro-Trp-Cys (SEQ ID NO:1), wherein $Xaa_1$ is Gly or des-$Xaa_1$, $Xaa_2$ is Pro or 4-trans-hydroxyproline and $Xaa_3$ is D-Trp or L-Trp, preferably D-Trp. The present invention is further directed to the peptides contryphan R and des-$Gly^1$ contryphan R. In contryphan R, $Xaa_1$ is Gly and $Xaa_3$ is D-Trp. These contryphans are useful as anticonvulsant or neuroprotective agents.

BRIEF DESCRIPTION OF THE FIGURES

FIG. 1. Purification of contryphan. (A) HPLC chromatogram of Conus radiatus venom sequentially extracted with 10 ml each of $H_2O$, 20%, 40% and 60% acetonitrile (ACN). Five milliliters of the combined extract from 500 mg of lyophilized venom was applied onto a $C_{18}$ semi-preparative column and eluted at 5 ml/min using a linear gradient of ACN in 0.085% trifluoroacetic acid (TFA) (0.45% rise in ACN/min). The peaks corresponding to contryphan ("R") and des-($Gly^1$)-contryphan ("$R_1$") are indicated by arrows. (B) HPLC chromatogram showing the purification of contryphan. The bioactive fraction obtained from HPLC of crude venom extract was applied onto a $C_{18}$ analytical column and eluted at 1 ml/min using a linear gradient of ACN in 0.085% TFA (0.09% rise in ACN/min). (C) The peak was repurified at 1 ml/min with a gradient of 0.9% rise in ACN/min. (D) HPLC chromatogram showing the purification of des-($Gly^1$)-contryphan. The bioactive fraction obtained from an HPLC of crude venom extract was applied into $C_{18}$ analytical column at 1 ml/min using a linear gradient of ACN in 0.085% TFA (0.09% rise in ACN/min). (E) The peak indicated by the arrow in D was repurified at 1 ml/min at a gradient of 0.9% rise in ACN/min.

FIG. 2. HPLC co-elution of synthetic and naturally occurring contryphan. Gradients are represented by dotted lines showing the rise in % of buffer B (90% ACN, 0.085% TFA). (A) Linear forms of synthetic peptide and contryphan reduced with dithiothreitol (DTT) (1.25% increase in buffer B/min). (B) Oxidized form of synthetic peptide with native contryphan (1% increase in buffer B/min).

FIG. 3. Reverse-phase HPLC chromatograms of contryphan and analogs. (a) Contryphan; (b) (D-$Trp^7$)-contryphan; (c) (L-$Trp^4$,D-$Trp^7$)-contryphan; (d) (L-$Trp^4$)-contryphan. Peptides were applied to a $C_{18}$ analytical column (Vydac, 218TP54, 4.6 mm×250 mm) and eluted using a linear gradient from 13.5% to 40.5% ACN in 0.08% TFA. Peaks are labeled with the apparent percent ACN at which elution occurred, calculated from the elution time. The elution position of contryphan relative to its analogs is indicated by the dotted line. Mixing experiments (not shown) demonstrate that authentic contryphan is well resolved from the all-L, D-$Trp^7$ or L-$Trp^4$,D-$Trp^7$ homologs, but the three homologs are not well resolved from each other under these elution conditions.

DETAILED DESCRIPTION OF THE PREFERRED EMBODIMENT

The present invention is directed to contryphan peptides having 6–12 amino acids, preferably including one or more D-tryptophan residues. More specifically, the present invention is directed to contryphan peptides having the general formula $Xaa_1$-Cys-$Xaa_2$-$Xaa_3$-Glu-Pro-Trp-Cys (SEQ ID NO: 1), wherein $Xaa_1$ is Gly or des-$Xaa_1$, $Xaa_2$ is Pro or 4-trans-hydroxyproline and $Xaa_3$ is D-Trp or L-Trp, preferably D-Trp. The present invention is further directed to the peptides contryphan R and des-$Gly^1$ contryphan R. In contryphan R, $Xaa_1$ is Gly and $Xaa_3$ is D-Trp. These contryphans are useful as anticonvulsant or neuroprotective agents.

The contryphans preferably have a D-tryptophan residue. This is the first report of D-tryptophan being formed through post-translational modification in the Conus snails. Furthermore, in contrast to all of the small D-amino acid-containing peptides previously reported, the contryphans isolated to date do not have the D-amino acid in position 2. Like most peptides found in Conus venoms, contryphan is crosslinked by a disulfide bond. The discovery and characterization of contryphan indicates that the modification system for converting L- to D-amino acids evolved in Conus venom ducts differs significantly from the post-translational isomerization of an L- to a D-amino acid previously described for all other small peptides in both vertebrate, and previously characterized molluscan systems. In addition, analysis of a cDNA clone from a C. radiatus venom duct library encoding contryphan has shown that D-Trp is coded for by the standard codon for L-Trp.

These contryphans have anticonvulsant activity in Fringes audiogenic seizure susceptible mice and in syndrome-specific seizure animal models. The contryphans are useful as anticonvulsant agents, as neuroprotective agents, for managing pain and for treating neurodegenerative disorders, especially those resulting from an overstimulation of excitatory amino acid receptors. Thus, the contryphans of the present invention are useful for the treatment and alleviation of epilepsy and as a general anticonvulsant agent. The contryphans are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events. The contryphans are further useful for the treatment of Alzheimer's disease, senile dementia, Amyotrophic Lateral Sclerosis, Parkinson's disease, Huntington's disease, Down's Syndrome, Korsakoff's disease, schizophrenia, AIDS dementia, multi-infarct dementia, and neuronal damage associated with uncontrolled seizures. The contryphans are further useful in controlling pain and are effective in the treatment of migraine. They can be used prophylactically or to relieve the symptoms associated with a migraine episode.

These peptides are sufficiently small to be chemically synthesized. General chemical syntheses for preparing the foregoing contryphan peptides are described hereinafter, along with specific chemical synthesis of one contryphan and indications of biological activities of these synthetic products. Various ones of these contryphan peptides can also be obtained by isolation and purification from specific Conus species using the technique described in U.S. Pat. No. 4,447,356 (Olivera et al., 1984), the disclosure of which is incorporated herein by reference.

Although the contryphan peptides of the present invention can be obtained by purification from cone snails, because the amounts of contryphan peptides obtainable from individual snails are very small, the desired substantially pure contryphan peptides are best practically obtained in commercially valuable amounts by chemical synthesis using solid-phase strategy. For example, the yield from a single cone snail may be about 10 micrograms or less of contryphan peptide. By "substantially pure" is meant that the peptide is present in the substantial absence of other biological molecules of the same type; it is preferably present in an amount of at least about 85% purity and preferably at least about 95% purity. Chemical synthesis of biologically active contryphan peptides depends of course upon correct determination of the amino acid sequence.

The contryphan peptides can also be produced by recombinant DNA techniques well known in the art. Such techniques are described by Sambrook et al. (1979). The peptides produced in this manner are isolated, reduced if necessary, and oxidized to form the correct disulfide bonds.

One method of forming disulfide bonds in the contryphan peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent contryphan molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide (DCC) or diisopropylcarbonyldimidazole, various active esters, e.g., esters of N-hydroxyphthalimide or N-hydroxysuccinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart et al. (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH-BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in dimethylformamide (DMF) at about 60° C. for 24 hours with stirring, when a peptide having free acid at the C-terminus is to be synthesized. Following the coupling of the Boc-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining (α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of hydroxybenzotriazole (HOBt) or HOAt).

The activating reagents used in the solid phase synthesis of the peptides are well known in the peptide art. Examples of suitable activating reagents are carbodiimides, such as NN'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxymethylated resin or a chloromethylated resin support by arnmonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above. A suitable method for cyclization is the method described by Cartier et al. (1996).

The contryphans are antagonists of the NMDA receptor sites and are useful as anticonvulsant agents, as neuroprotective agents, for managing pain and for treating neurodegenerative disorders, especially those resulting from an overstimulation of excitatory amino acid receptors. Thus, the contryphans of the present invention are useful for the treatment and alleviation of epilepsy and as a general anticonvulsant agent. The use of contryphans in these conditions includes the administration of a contryphan in a therapeutically effective amount to patients in need of treatment. The contryphans can be used to treat the seizures to reduce their effects and to prevent seizures. The contryphans are also useful to reduce neurotoxic injury associated with conditions of hypoxia, anoxia or ischemia which typically follows stroke, cerebrovascular accident, brain or spinal chord trauma, myocardial infarct, physical trauma, drownings, suffocation, perinatal asphyxia, or hypoglycemic events. To reduce neurotoxic injury, the contryphans should be administered to the patient within 24 hours of the onset of the hypoxic, anoxic or ischemic condition in order for the contryphans to effectively minimize the CNS damage which the patient will experience.

The contryphans are further useful for the treatment of Alzheimer's disease, senile dementia, Amyotrophic Lateral Sclerosis, Parkinson's disease, Huntington's disease, Down's Syndrome, Korsakoff's disease, schizophrenia, AIDS dementia, multi-infarct dementia, and neuronal damage associated with uncontrolled seizures. The administration of the contryphans to a patient experiencing such conditions will serve to either prevent the patient form experiencing further neurodegeneration or it will decrease the rate at which neurodegeneration occurs. The contryphans are further useful in controlling pain and are effective in the treatment of migraine. They can be used prophylactically or to relieve the symptoms associated with a migraine episode.

The anticonvulsant effects of contryphans have been demonstrated in animal models. In rodents, contryphans are effective against supramaximal tonic extension seizures produced by maximal electroshock and threshold seizures induced by s.c. pentylenetetrazol or picrotoxin. Contryphans are also effective against focal seizures induced by aluminum hydroxide injection into the pre- and post-central gyri of rhesus monkeys. Contryphans when administered to patients with refractory complex partial seizures may markedly reduced seizure frequency and severity. Moreover, the clinical utility of contryphans as a therapeutic agent for epilepsy may include generalized tonic-clonic and complex partial seizures.

Studies in laboratory animal models demonstrate the neuroprotectant properties of contryphans. Contryphans protect against hypoxic damage to the hippocampal slice in vitro. In neonate rats, contryphans reduce the size of cortical infarcts and amount of hippocampal necrosis following bilateral carotid ligation and hypoxia. The contryphans may also be effective anti-pain agents.

For newly diagnosed patients with a seizure disorder and patients with seizure disorders for whom changes in drugs are being made, a relatively low dosage of drug is started and increased over a week or so to a standard therapeutic dosage. After about a week at such dosage, blood levels are obtained to determine the patient's pharnacokinetic response and, if appropriate, whether the effective therapeutic level has been reached. If seizures continue, the daily dosage is increased by small increments as dosage rises above the usual. Once seizures are brought under control, the drug should be continued without interruption at least one seizure-free year. At that time, discontinuation of the drug should be considered, since about 50% of such patients will remain seizure free without drugs. Patients whose attacks initially were difficult to control, those who failed a therapy-free trial and those with important social reasons for avoiding seizures should be treated indefinitely.

Pharmaceutical compositions containing a compound of the present invention as the active ingredient can be prepared according to conventional pharmaceutical compounding techniques. See, for example, *Remington's Pharmaceutical Sciences,* 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The contryphans can also be administered in a cell based delivery system in which a DNA sequence encoding a contryphan is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. The DNA sequence can be isolated from cDNA libraries using degenerate probes based on the sequences of the contryphans disclosed herein or amplified from these libraries using appropriate degenerate primers. Alternatively, suitable DNA sequences can be prepared synthetically for each of the disclosed contryphan on the basis of the disclosed sequences and the known genetic code.

The contryphans are administered in an amount sufficient to antagonize the effects of excitatory amino acids or other agonists upon the NMDA receptor complex. The dosage range at which these contryphans exhibit this antagonistic effect can vary widely depending upon the particular disease being treated, the severity of the patient's disease, the patient, the specific contryphan being administered, the route of administration and the presence of other underlying disease states within the patient. Typically the contryphans exhibit their therapeutic effect at a dosage range from about 0.015 mg/kg to about 200 mg/kg, preferably from about 0.02 mg/kg to about 100 mg/kg of the active ingredient, more preferably from about 0.03 mg/kg to about 75 mg/kg of the active ingredient, and most preferably from about 0.03 mg/kg to about 50 mg/kg of the active ingredient. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form.

EXAMPLES

The present invention is described by reference to the following Examples, which are offered by way of illustration and are not intended to limit the invention in any manner. Standard techniques well known in the art or the techniques specifically described below were utilized.

Example 1

Methods

Preparation of venom extract. Specimens of *Conus radiatus* were obtained from the Philippines. The venom ducts were dissected from the cone snails and the venom was squeezed out of the ducts as previously described (Cruz, 1976). The collected venom was lyophilized and stored in the freezer. Five hundred milligrams of lyophilized venom was sequentially extracted with 10 ml each of water, 20% acetonitrile, 40% acetonitrile and 60% acetonitrile. The venom suspension was sonicated in the extracting solvent for three 30 sec periods over ice water and centrifuged at 5000×g for 5 min. The combined supernates were stored at −20° C. for further purification.

Purification of peptides. Crude venom extract was applied onto a Vydac $C_{18}$ semi-preparative column (10×250 mm) and eluted with a linear gradient of acetonitrile in 0.085% TFA at 5 ml/min. Further purifications of bioactive peaks were done on a Vydac $C_{18}$ analytical column (4.6×250 mm) eluted with the acetonitrile/TFA system at 1 ml/min. The effluents were monitored at 220 nm. Peaks were collected in polypropylene tubes and aliquots were assayed for biological activity.

Bioassay. Biological activity was assayed by intracranial injection in mice (9 to 21 days old). Aliquots (20–30 μl) of peptide in normal saline were injected using a 0.3 ml syringe with a 29-gauge needle. Each control mouse was injected with an equal volume of normal saline solution containing dissolved residue of lyophilized column buffer. After injection, the mice were placed in cages for observation.

Peptide sequencing. The peptide was reduced and alkylated prior to sequencing. The pH of the peptide solution was raised to 7–8 by adding 0.5 M Tris base before dithiothreitol was added to a final concentration of 10 mM. The solution was flushed with nitrogen, incubated at 65° C. for 20 min and cooled to room temperature. Three microliters of 4-vinylpyridine were added per 500 ml of solution. The mixture was left in the dark for 25 min at room temperature then diluted with 0.1% TFA and applied onto a Vydac $C_{18}$ analytical HPLC column.

The purified peptide was sequenced by automated Edman degradation (Edman & Begg, 1967) on an Applied Biosystems 477A Protein Sequencer with a 120A Analyzer (DNA/Peptide Facility, University of Utah). The 3-phenyl-2-thiohydantoin (PTH) derivatives were identified by HPLC. The predicted mass of the peptide was compared with the molecular masses obtained by Dr. Anthony Craig of the Salk Institute for Biological Studies using laser desorption mass spectrometry (LDMS) and liquid secondary ionization mass spectrometry (LSIMS). The LSIMS samples were measured at 3000 resolution from a glycerol matrix.

Peptide synthesis. The protected peptide resin was synthesized using standard Fmoc chemistry and couplings using equimolar amounts of amino acid derivatives DCC and HOBT. Some amino acid side chains were protected as follows: Cys (trityl), OH-Pro (t-butyl) and Glu (t-butyl).

After synthesis, the terminal Fmoc group was removed by treatment with 1:4 piperidine:N-methylpyrrolidone (v/v). The peptide was cleaved from the resin by treatment with TFA/$H_2O$/ethanedithiol/phenol/thioanisole (80/5/2.5/7.5/5 by volume) for 1.5 hr at room temperature. The mixture was filtered under vacuum into t-butylmethylether at −10° C. Linear peptide was collected by centrifugation at 5000×g for 5 min and washed with t-butylmethyl ether. The pellet was dissolved in 20% acetonitrile containing 0.1% TFA and applied into a Vydac $C_{18}$ preparative column (25×250 mm). Elution was carried out at 20 ml/min using a gradient of acetonitrile in 0.1% TFA. The major peptide-containing fraction was oxidized with 1 mM iodine in 0.1% TFA/20% acetonitrile (Gray, 1993), then the reaction was quenched with a few drops of 0.1 M ascorbic acid. The oxidized peptide was purified by HPLC.

Example 2

Purification of Contryphan-R

Figure 1A:
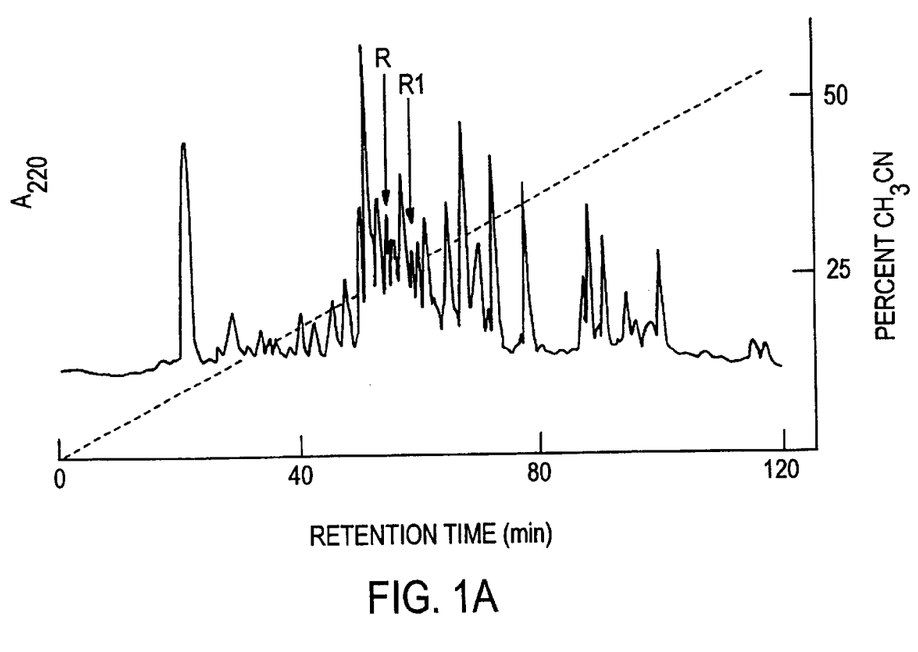
Figure 1B:
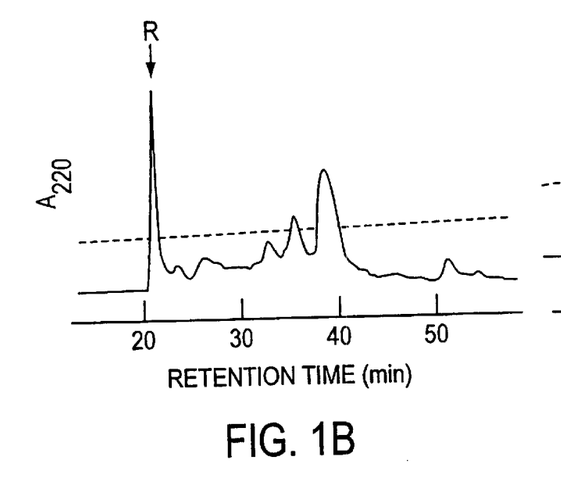
Figure 1C:
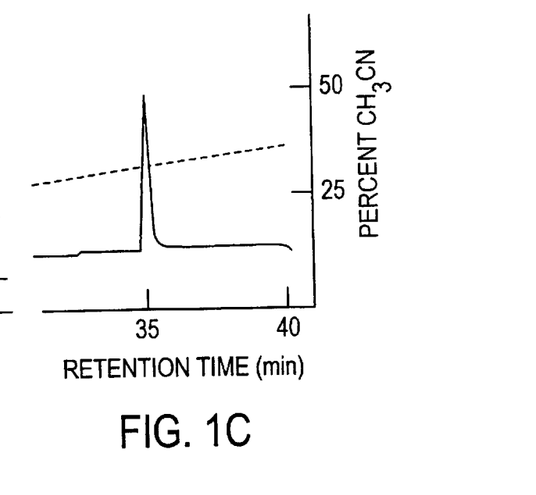
Figure 1D:
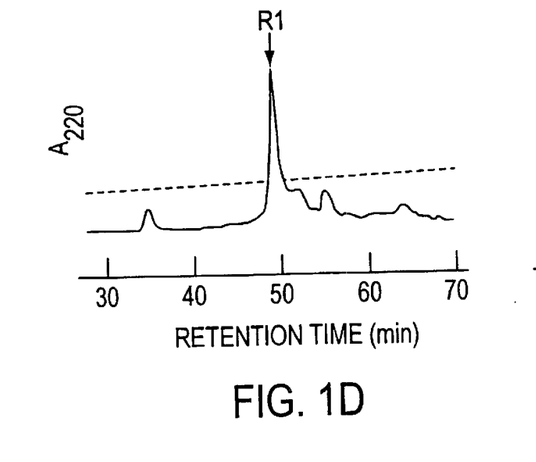
Figure 1E:
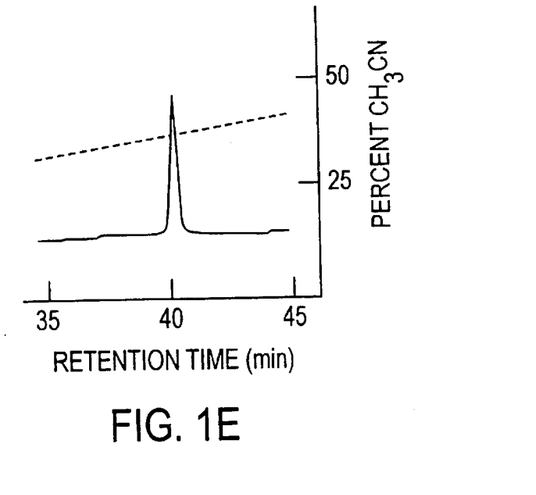

Crude venom was obtained from specimens of *Conus radiatus* collected from Manila Bay and Marinduque. The crude venom extract prepared as described in Example 1 was applied to a $C_{18}$ semi-preparative column, using a gradient of 0.45% $CH_3CN$ per min. A complicated HPLC profile (FIG. 1A), typical of Conus venoms was obtained. As shown in Table 1, when injected intracranially in mice as described in Example 1, material from the several peaks (indicated by arrows) caused mild excitatory symptoms at low doses with tail raising and severe symptoms including "barrel rolling" and seizure observed with increasing dosages.

TABLE 1

Bioactivity of Contryphan

| Dose | Activity |
|---|---|
| Low: 0.5–2.5 nmole/g | Grooming, licking and biting of paws, occasional occasional tail-raising, occasional hyperactivity. |
| Medium: 4–6 nmole/g | stiffening and raising of tail to almost perpendicular to body; "barrel-rolling", and subsequent passivity. |
| High: 8–20 nmole/g | Paralysis of extremities, circular motion, "barrel-rolling", seizure and death. |

The peak designated as R was resolved into several peaks on HPLC in a $C_{18}$ analytical column eluted with a very slow gradient of acetonitrile. The first major peak which showed the same activity as the R peak of panel A was rechromatographed to give a homogeneous peak shown in panel C. Similar HPLC runs of the R1 peak of panel A gave the profile in panel D; rechromatography of this peak gave a homogeneous peptide.

Example 3

Biochemical Characterization and Biological Activity of Contryphan and its des-(Gly$^1$) Derivative The purified peptides were reduced, alkylated and sequenced as described in Example 1. The amino acid sequence obtained for peak R is shown Table 2. The calculated MH$^+$ value (990.4) assumes that the Cys residues form a disulfide, and an amidated C-terminal residue.

TABLE 2

Sequence Analysis of Contryphan

| | Peak R | |
|---|---|---|
| Cycle | Assigned Residue | Yield (pmol) |
| 1 | G | 83.6 |
| 2 | C | 106.0 |
| 3 | O | 91.3 |
| 4 | W | 7.7 |
| 5 | E | 23.8 |
| 6 | P | 13.2 |
| 7 | W | 1.6 |
| 8 | C | 4.9 |

Because of the high tryptophan content of this peptide, it was designated "contryphan." Peptide R1 had an identical sequence except that it lacks the N-terminal Gly residue. Thus, the amino acid sequences of the two peptides are:

| | |
|---|---|
| Contryphan R | GCOWEPWC-NH$_2$ (SEQ ID NO:2) |
| des-(Gly$^1$)-Contryphan R | COWEPWC-NH$_2$ (SEQ ID NO:3) |

Liquid secondary ionization mass spectrometry of the native contryphan R peptide gave a monoisotopic MH$^+$ of 990.3 (calculated MH$^+$=990.4) and a monoisotopic MH$^+$ of 933.3 (calculated MH$^+$=933.3) for des-(Gly$^1$)-contryphan R. These values are consistent with the amino acid sequences assigned with the Cys residues present as disulfides and the C-termini as amide groups.

Example 4

Synthesis of Contryphans and L-derivatives

Figure 2A:
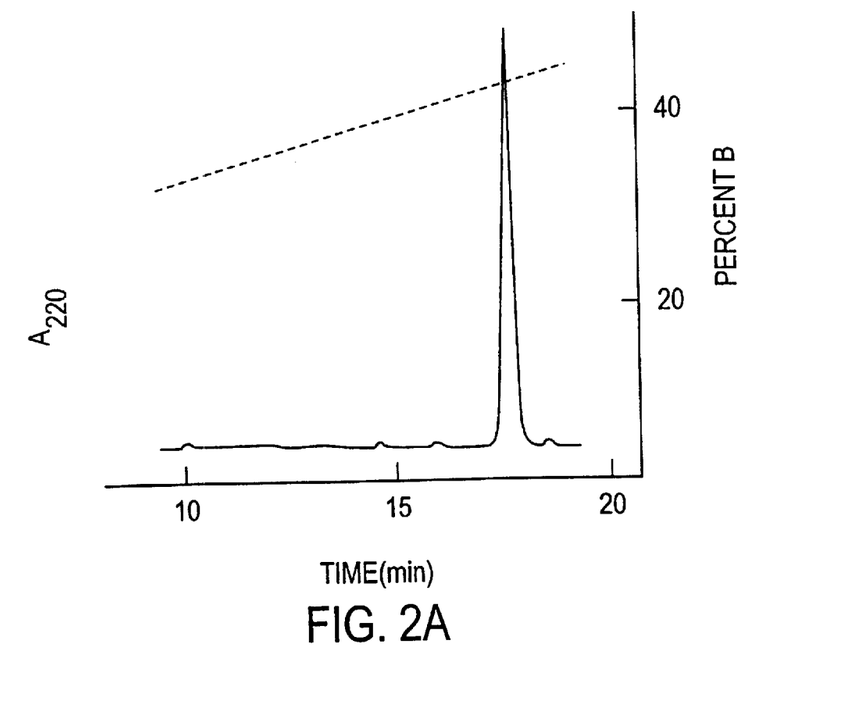
Figure 2B:
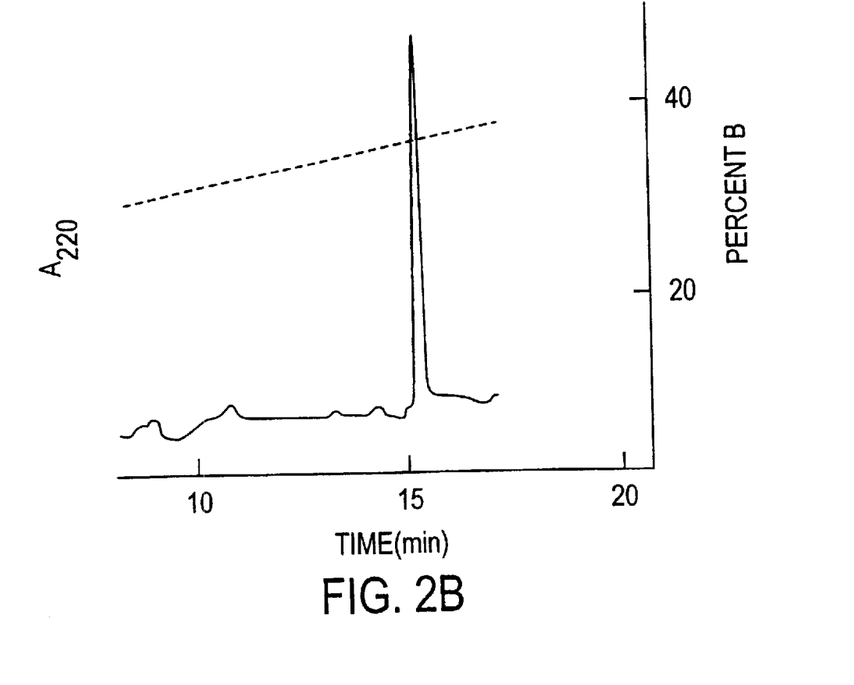
Figure 3:
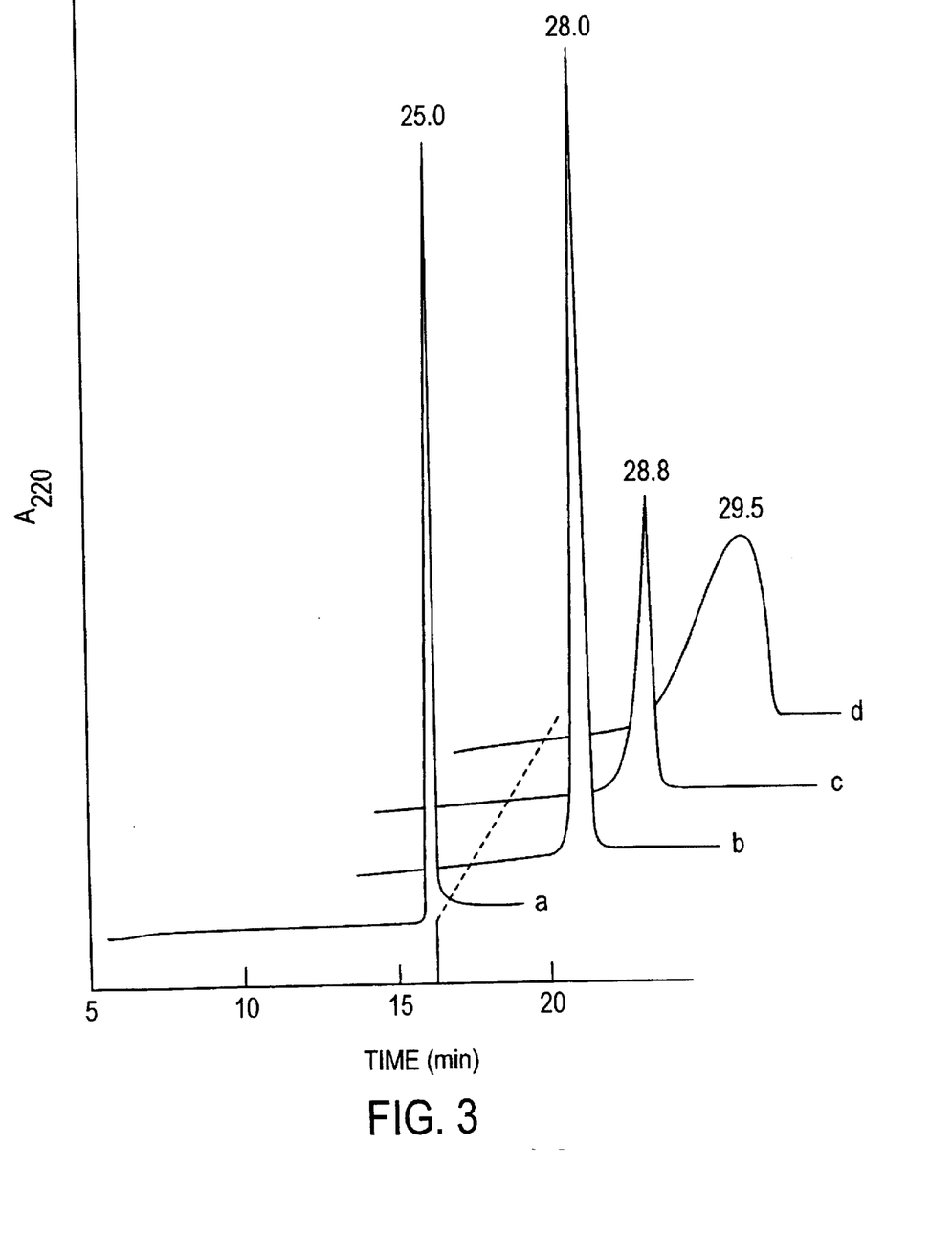

To independently verify the sequence, synthetic peptides containing standard L-amino acids were prepared as described in Example 1. However, the synthetic peptides did not co-elute with native contryphan. The all-L analog of contryphan showed an unusually broad HPLC peak and it appeared to be less stable than the native peptide; flushing the synthetic peptide solution with nitrogen seemed to retard its degradation to a purple derivative. Because of the identical mass of the native and synthetic L-amino acid-containing peptide, synthetic peptide homologs containing D-tryptophan at positions 4 and 7 of contryphan were synthesized. Both the fully reduced and the oxidized/folded forms of the synthetic D-Trp$^4$ peptide co-eluted with the corresponding forms of the natural peptide (FIG. 2). The D-Trp$^{4,7}$ and D-Trp$^7$ analogs did not co-elute with native contryphan (FIG. 3). The presence of D-tryptophan in position 3 of des-(Gly$^1$)-contryphan was also confirmed by chemical synthesis and co-elution of native and synthetic material.

On i.c. injection into mice, synthetic contryphan R elicited identical symptomatology to the native material (tail raising and hyperactivity) at low doses. Surprisingly, the all-L analog, (L-Trp$^4$)-contryphan R, shows a similar activity whereas D-(Trp$^7$)-contryphan R elicited no detectable activity (>10 nmol/g body weight). Des-(Gly$^1$)-contryphan R elicited similar symptoms to contryphan R but appears to be less potent; even at the highest doses (20 nmoles/g), the peptide did not cause any lethality.

Example 5

In vivo Activity of Contryphans in Frings Audiogenic Seizure Susceptible Mice In vivo anticonvulsant activity of contryphan R is analyzed in Frings audiogenic seizure susceptible mice as described by White et al. (1992). Contryphan R has anticonvulsant activity.

Example 6

In Vivo Activity of Contryphans in CF No. 1 Mice

In vivo anticonvulsant activity of contryphan R is analyzed in CF No. 1 mice as described by White et al. (1995), using the maximal electroshock, subcutaneous pentylenetetrazol (Metrazol) seizure threshold and threshold tonic extension test. Contryphan R has anticonvulsant activity.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Abiko, H. et al. (1986). Protective effect of phenytoin and enhancement of its action by combined administration of mannitol and vitamin E in cerebral ischemia. *Brain Res.* 38:328–335.

Aldrete, J. A. et al. (1979). Effect of pretreatment with thiopental and phenytoin on postischemic brain damage in rabbits. *Crit. Care Med.* 7:466–470.

Ascher, P. and Nowak, L. (1986). Calcium permeation of the channels activated by N-methyl-D-aspartate (NMDA) in mouse central neurons. *J. Physiol.* 377:35p.

Bodansky et al. (1966). *Chem. Ind.* 38:1597–98.

Bowyer, J. F. (1982). Phencyclidine inhibition of the rate of kindling development. *Esp. Neurol.* 75:173–175.

Cartier, G. E. et al. (1996). *J. Biol. Chem.* 271:7522–7528.

Chandler, P. et al. (1993). Polyamine-like Actions of Peptides Derived from Contryphan-G, an N-methyl-D-aspartate (NMDA) Antagonist. *J. Biol. Chem.* 268:17173–17178.

Cline, H. T. et al. (1987). N-Methyl-D-aspartate receptor antagonist desegregates eye-specific stripes. *Proc. Natl. Acad. Sci. USA* 84:4342–4345.

Collinridge, G. L. et al. (1983). Excitatory amino acids in synaptic transmission in the Schaffer collateral-commissural pathway of the rat hippocampus. *J. Physiol.* 334:3446.

Cruz, L. J. et al. (1976). *Veliger* 18, 302–308

Cruz, L. J. et al. (1987). Conus geographus toxins that discriminate between neuronal and muscle sodium channels. *J. Biol. Chem.* 260:9280–9288.

Doyle, D. D. et al. (1993). Divalent cation competition with [$^3$H]saxitoxin binding to tetrodotoxin-resistant and -sensitive sodium channels. *J. Gen. Physiol* 101:153–182.

Dudley, S. C. et al. (1995). A $\mu$-Conotoxin-Insensitive Na$^+$ Channel Mutant: Possible Localization of a Binding Site at the Outer Vestibule. *Biophys. J.* 69:1657–1665.

Edman, P. and Begg, G. (1967). *Eur. J. Biochem.* 1, 80–91

Fujisawa, I. et al. (1992). *Comp. Biochem. Physiol.* (C) 102, 91–95.

Gray, W. R. (1993). Disulfide Structures of Highly Bridged Peptides: A New Strategy for Analysis. *Protein Science* 2:1732–1748.

Haack, J. A. et al. (1990). Contryphan-T: a gamma-carboxyglutamate containing peptide with N-methyl-d-aspartate antagonist activity. *J Biol. Chem.* 265:6025–6029.

Harris, E. W. et al. (1984). Long-term potentiation in the hippocampus involves activation of N-methyl-D-aspartate receptors. *Brain Res.* 323:132–137.

Horiki, K. et al. (1978). *Chemistry Letters* 165–68.

Johnson, J. W. and Ascher, P. (1987). Glycine potentiates the NMDA response in cultured mouse brain neurons. *Nature* 325:529–531.

Kaiser et al. (1970). *Anal. Biochem.* 34:595.

Kamatani, Y. et al. (1989). *Biochem. Biophys. Res. Comm.* 160, 1015–1020

Kapoor (1970). *J. Pharm. Sci.* 59:1–27.

Kleckner, N. W. and Dingledine, R. D. (1988). Requirement for glycine inactivation of NMDA receptors expressed in Xenopus oocytes. *Science* 241:835–837.

Kornreich, W. D. et al. (1986). U.S. Pat. No. 4,569,967.

Kreil, G. (1994). *J. Biol. Chem.* 269:10967–10970.

Mayer, M. L. et al. (1987). Agonist- and voltage-gated calcium entry in cultured mouse spinal cord neurons under voltage clamp measured using arsenazo III. *J. Neurosci.* 7:3230–3244.

Mena, E. E. et al. (1990). Contryphan-G: a novel peptide antagonist to the N-methyl-D-aspartic acid (NMDA) receptor. *Neurosci. Lett.* 118:241–244.

McNamara, J. O. et al. (1988). Anticonvulsant and antiepileptogenic action of MK-801 in the kindling and electroshock models. *Neuropharmacology* 27:563–568.

*The Merck Manual of Diagnosis and Therapy*, 16 Ed., Berkow, R. et al., eds., Merck Research Laboratories, Rahway, N.J., pp. 1436–1445 (1992).

*Methoden der Organischen Chemie (Houben-Weyl): Synthese von Peptiden,* E. Wunsch (Ed.), Georg Thieme Verlag, Stuttgart, Ger. (1974).

Monteccuchi, P. C. et al. (1981). *Int. J. Pept. Prot. Res.* 17:275–283.

Morris, R. G. M. et al. (1986). Selective impairment and blockade of long-term potentiation by an N-methyl-D-aspartate receptor antagonist, AP5. *Nature* 319:774–776.

Nehlig, A. et al. (1990). Effects of phenobarbital in the developing rat brain. In *Neonatal Seizures*, Wasterlain, C. G. and Vertt, P. (eds.), Raven Press, New York, pp. 285–194.

Nishiuchi, Y. et al. (1993). Synthesis of gamma-carboxyglutamic acid-containing peptides by the Boc strategy. *Int. J. Pept. Protein Res.* 42:533–538.

Nowak, L. et al. (1984). Magnesium gates glutamic-activated channels in mouse central neurons. *Nature* 307:462–465.

Ohta, N. et al. (1991). *Biochem. Biophys. Res. Commun.* 178, 486–493

Olivera, B. M. et al. (1984). U.S. Pat. No. 4,447,356.

Olivera, B. M. et al. (1985). Peptide neurotoxins from fish-hunting cone snails. *Science* 230:1338.

Park, C. K. et al. (1988). The glutamate antagonist MK-801 reduces focal ischemia brain damage in the rat. *Ann. Neurol.* 24:543–551.

Rall T. W. and Schleifer, L. S. in *Goodman and Gilman's The Pharmacological Basis of Therapeutics*, Seventh Ed., Gilman, A. G. et al., eds., Macmillan Publishing Co., New York, pp. 446–472 (1985).

*Remington's Pharmaceutical Sciences*, 18th Ed., Mack Publishing Co., Easton, Pa. (1990).

Reynolds, I. J. et al. (1987). $^3$H-Labeled MK-801 binding to excitatory amino acid receptor complex from rat brain is enhance by glycine. *Proc. Natl. Acad Sci. USA* 84:7744–7748.

Richter, K. et al. (1987). *Science* 238:200–202.

Richter, K. et al. (1990). *Proc. Natl. Acad. Sci. USA* 87, 4836–4839.

Rivier, J. R. et al. (1978). *Biopolymers* 17:1927–38.

Rivier, J. R. et al. (1987). Total synthesis and further characterization of the gamma-carboxyglutamate-containing 'sleeper' peptide from *Conus geographus*. *Biochem.* 26:8508.

Sambrook, J. et al. (1979). *Molecular Cloning: A Laboratory Manual*, 2nd Ed., Cold Spring Harbor Laboratory, Cold Spring Harbor, N.Y.

Schroder & Lubke (1965). *The Peptides* 1:72–75, Academic Press, N.Y.

Shikata, Y. et al. (1995). *J. Biol. Chem.* 270, 16719–16723

Simon, R. P. et al. (1984). Blockade of N-methyl-D-aspartate receptors may protect against ischemic damage in the brain. *Science* 226:850–852.

Skolnick, P. et al. (1992). Noncompetitive Inhibition of N-Methyl-D-Aspartate by Contryphan-G: Evidence for an Allosteric Interaction at Polyamines Sites. *J. Neurochem.* 59:1526–1521.

Stewart and Young, *Solid-Phase Peptide Synthesis,* Freeman & Co., San Francisco, Calif. (1969).

Troupin, A. S. et al. (1986). MK-801. In *New Anticonvulsant Drugs, Current Problems in Epilepsy* 4, Meldrum, B. S. and Porter, R. J. (eds.), John Libbey, London, pp. 191–202.

Vale et al. (1978). U.S. Pat. No. 4,105,603.

White, H. S., et al. (1992). Anticonvulsant profile of MDL 27,266: an orally active, broad-spectrum anticonvulsant agent. *Epilepsy Res.* 12:217–226.

White, H. S., et al. (1995). Experimental Selection, Quantification, and Evaluation of Antiepileptic Drugs. In *Antiepileptic Drugs*, 4th Ed., Levy, R. H., eds., Raven Press, New York, pp. 99–110.

Williams, K. et al. (1991). Modulation of the NMDA receptor by polyarnines (Minireview). *Life Sci.* 48:469–498.

Wong, E. H. P. et al. (1986). The anticonvulsant MK-801 is a potent NMDA antagonist. *Proc. Natl. Acad. Sci. USA* 83:7104–7108.

Wroblewski, J. T. et al. (1989). Glycine and D-serine act a positive modulators of signal transduction at N-methyl-D-aspartate sensitive glutamate receptors in cultured cerebellar granule cells. *Neuropharmacology* 28:447–452.

Yasuda-Kamatani, Y. et al. (1995). *J. Neurochem.* 64, 2248–2255

Zhou L. M., et al. (1996a). Synthetic Analogues of Contryphan-G: NMDA Antagonists Acting Through a Novel Polyamine-Coupled Site. *J. Neurochem.* 66:620–628.

U.S. Pat. No. 3,972,859 (1976).
U.S. Pat. No. 3,842,067 (1974).
U.S. Pat. No. 3,862,925 (1975).
U.S. Pat. No. 5,550,050.
PCT Published Application WO 96/11698.
PCT Published Application No. WO 92/19195.
PCT Published Application No. WO 94/25503.
PCT Published Application No. WO 95/01203.
PCT Published Application No. WO 95/05452.
PCT Published Application No. WO 96/02286.
PCT Published Application No. WO 96/02646.
PCT Published Application No. WO 96/40871.
PCT Published Application No. WO 96/40959.
PCT Published Application No. WO 97/12635.

What is claimed is:

1. A substantially pure contryphan peptide of the generic formula:

$$Xaa_1\text{-Cys-}Xaa_2\text{-}Xaa_3\text{-Glu-Pro-Trp-Cys} \quad (\text{SEQ ID NO:1}),$$

wherein $Xaa_1$ is Gly or des-$Xaa_1$, $Xaa_2$ is Pro or 4-trans-hydroxyproline and $Xaa_3$ is D-Trp or L-Trp.

2. The contryphan peptide of claim 1 having the amino acid sequence Gly-Cys-$Xaa_2$-$Xaa_3$-Glu-Pro-Trp-Cys (SEQ ID NO:4).

3. The contryphan peptide of claim 1 having the amino acid sequence Cys-$Xaa_2$-$Xaa_3$-Glu-Pro-Trp-Cys (SEQ ID NO:5).

4. The contryphan peptide of claim 1, wherein $Xaa_3$ is L-Trp.

5. The contryphan peptide of claim 1, wherein $Xaa_3$ is D-Trp.

6. The contryphan peptide of claim 1, wherein $Xaa_2$ is 4-trans-hydroxyproline.

7. The contryphan peptide of claim 1, wherein $Xaa_2$ is proline.

8. The contryphan peptide of claim 1, wherein the carboxy terminus contains an amide group.

* * * * *